United States Patent
Ohta et al.

(10) Patent No.: US 7,308,315 B2
(45) Date of Patent: Dec. 11, 2007

(54) VISION REGENERATION ASSISTING APPARATUS

(75) Inventors: Jun Ohta, Nara (JP); Shigeru Nishimura, Chiba (JP); Kohtaro Idegami, Ishikawa (JP); Keiichiro Kagawa, Nara (JP)

(73) Assignee: Nidek Co., Ltd., Aichi (JP)

( * ) Notice: Subject to any disclaimer, the term of this patent is extended or adjusted under 35 U.S.C. 154(b) by 612 days.

(21) Appl. No.: 10/467,916

(22) PCT Filed: Feb. 14, 2002

(86) PCT No.: PCT/JP02/01255

§ 371 (c)(1),
(2), (4) Date: Jan. 23, 2004

(87) PCT Pub. No.: WO02/064072

PCT Pub. Date: Aug. 22, 2002

(65) Prior Publication Data

US 2004/0116980 A1 Jun. 17, 2004

(30) Foreign Application Priority Data

Feb. 15, 2001 (JP) .............................. 2001-039031
Sep. 4, 2001 (JP) .............................. 2001-267743

(51) Int. Cl.
*A61N 1/00* (2006.01)

(52) U.S. Cl. .......................... 607/54; 607/53; 623/6.63
(58) Field of Classification Search .................. 607/54, 607/53; 623/6.63

See application file for complete search history.

(56) References Cited

U.S. PATENT DOCUMENTS 5,106,179 A 4/1992 Kamaya et al.

(Continued)

FOREIGN PATENT DOCUMENTS

| JP | 2001-204757 A | 7/2001 |
|---|---|---|
| WO | WO 90/00912 A1 | 2/1990 |
| WO | WO 94/26209 A1 | 11/1994 |
| WO | WO 96/39221 A | 12/1996 |
| WO | WO 97/05922 A2 | 2/1997 |
| WO | WO 99/45870 A1 | 9/1999 |

*Primary Examiner*—Kristen Mullen
*Assistant Examiner*—Jon Eric Morales
(74) *Attorney, Agent, or Firm*—Sughrue Mion Pllc.

(57) ABSTRACT

It is an object of the invention to provide a vision regeneration assisting apparatus capable of assisting in vision regeneration without making a system structure complicated.

In the invention, a vision regeneration assisting apparatus for regenerating a vision of a patient going blind by a disease of a retina includes a photosensor embedded in the retina of an eye of the patient and converting an optical signal into an electric signal, photographing means for photographing an object to be recognized by the patient, image processing means for carrying out an image processing to extract a feature with respect to an image of the object obtained by the photographing means, pulse light forming means for forming a luminous flux into a pulse light to induce a vision, and irradiating means provided before the eye of the patient and applying the pulse light toward the photosensor so as to be formed as an image processed by the image processing means.

7 Claims, 6 Drawing Sheets

U.S. PATENT DOCUMENTS 5,159,927 A * 11/1992 Schmid .................. 607/53
5,836,996 A * 11/1998 Doorish .................. 623/6.63
5,895,415 A *  4/1999 Chow et al. ............. 607/54
6,032,062 A *  2/2000 Nisch .................... 600/372
6,458,157 B1 * 10/2002 Suaning ................. 623/6.63
2002/0038134 A1 * 3/2002 Greenberg et al. ....... 607/1

* cited by examiner

VISION REGENERATION ASSISTING APPARATUS

This application claims priority from Japan Application No. 2001-039031, filed on Feb. 15, 2001 and Japan Application No. 2001-267743, filed on Sep. 4, 2001.

TECHNICAL FIELD

The present invention relates to a vision regeneration assisting apparatus in which a photodiode is embedded under a retina to artificially give a vision signal.

BACKGROUND ART

A disease such as retinitis pigmentosa or age-related macular degeneration causes a vision handicap, and vision is sometimes lost when the disease becomes worse. Usually, when light is applied to a retina, an optical signal is converted into an electric signal in a photoreceptor cell, and the electric signal is changed into a pulse signal in a ganglion cell and the pulse signal is transmitted to a brain. When the disease such as the retinitis pigmentosa or the age-related macular degeneration is generated, the photoreceptor cell is decreased or becomes extinct. For this reason, the optical signal cannot be converted into the electric signal so that vision cannot be obtained. In recent years, various trials for recovering vision have been proposed for such loss of the vision. For example, JP-T-11-506662 has disclosed the invention related to the generation of vision which uses a retina stimulating system.

The system serves to embed, under a retina, a microphotodiode having sensitivity to visible light and infrared light and to receive, into the microphotodiode, an image (video) amplified and modulated by a neuron net computer through a CCD camera, thereby obtaining vision.

In the retina stimulating system, however, the visible light and the infrared light are used for light incident on a photodiode. Therefore, it is necessary to cause the photodiode to be a complicated mechanism. Moreover, the system itself has a complicated structure.

In consideration of the problems of the prior art described above, it is a technical object to provide a vision regeneration assisting apparatus capable of assisting in vision regeneration without making a system structure complicated.

DISCLOSURE OF THE INVENTION

In order to attain the object, the invention is characterized by the following structure.

(1) A vision regeneration assisting apparatus for regenerating vision of a patient going blind by a disease of a retina is characterized by a photosensor embedded in the retina of an eye of the patient and for converting an optical signal into an electric signal, photographing means for photographing an object to be recognized by the patient, image processing means for carrying out image processing to extract a feature for an image of the photographed object, irradiating means provided before the eye of the patient and for applying pulse light to the photosensor, and control means for controlling the irradiating means based on image information subjected to the image processing.

(2) The vision regeneration assisting apparatus according to the (1) is characterized in that the irradiating means includes scanning means for two-dimensionally scanning light over the photosensor, and the control means controls driving operation of the scanning means based on image information.

(3) The vision regeneration assisting apparatus according to the (2) is characterized in that the control means controls a repetitive frequency of scan.

(4) The vision regeneration assisting apparatus according to the (1) is characterized in that the irradiating means includes a digital micromirror device, and the control means controls driving operation of the digital micromirror device based on the image information.

(5) The vision regeneration assisting apparatus according to the (1) is characterized in that the irradiating means includes display means in which a large number of LEDs are arranged, and the control means controls driving operation of the display means based on image information.

(6) The vision regeneration assisting apparatus according to the (1) is characterized in that the image processing means extracts only a contour of the image of the photographed object as image information by the image processing, and the control means controls the irradiating means based on the image information thus extracted.

(7) The vision regeneration assisting apparatus according to the (1) is characterized in that a plurality of photosensors are embedded in the retina of the eye of the patient and an embedding interval between the photosensors is smaller than a spot diameter of light on the photosensor.

(8) The vision regeneration assisting apparatus according to the (1) is further characterized by changing means for changing an irradiating condition of light by the irradiating means, the control means controlling the irradiating means based on the irradiating condition thus changed.

(9) The vision regeneration assisting apparatus according to the (1) is further characterized by projecting means for projecting a predetermined pattern onto the object.

(10) The vision regeneration assisting apparatus according to the (1) is characterized in that the irradiating means applies a pulse light, and the control means controls at least one of a frequency and an amplitude of a pulse based on the image information.

Figure 1:
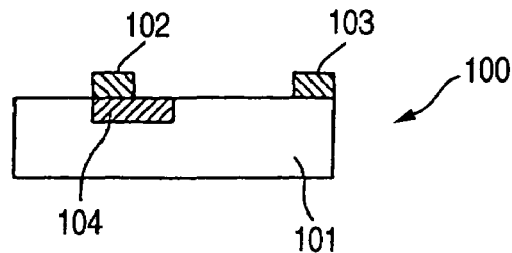
FIG. 1 is a view showing the schematic structure of a microphotodiode to be used in an embodiment of the invention.

In the drawings, 1 denotes an irradiating device body, 10 denotes a photographing unit, 13 denotes a CCD camera, 14 denotes an LED, 16 denotes a mirror, 16a denotes a motor, 17 denotes a mirror, 17a denotes a motor, 20 denotes a video processing unit, 30 denotes a response unit, and 100 denotes a microphotodiode.

BEST MODE FOR CARRYING OUT THE INVENTION

An embodiment of the invention will be described with reference to the drawings. A vision regeneration assisting apparatus to be used in the embodiment comprises a microphotodiode to be embedded in the retina of a patient and an irradiating device for applying a luminous flux (light beam) having a directivity to the microphotodiode.

FIG. 1 is a view showing the schematic structure of the microphotodiode to be a kind of photosensor to be embedded in a retina.

100 denotes a microphotodiode. As shown in the drawing, the microphotodiode 100 comprises an n-type electrode 102 provided on an n-type diffusion layer 104 and a p-type electrode 103 provided on a p-type substrate 101.

Figure 2:
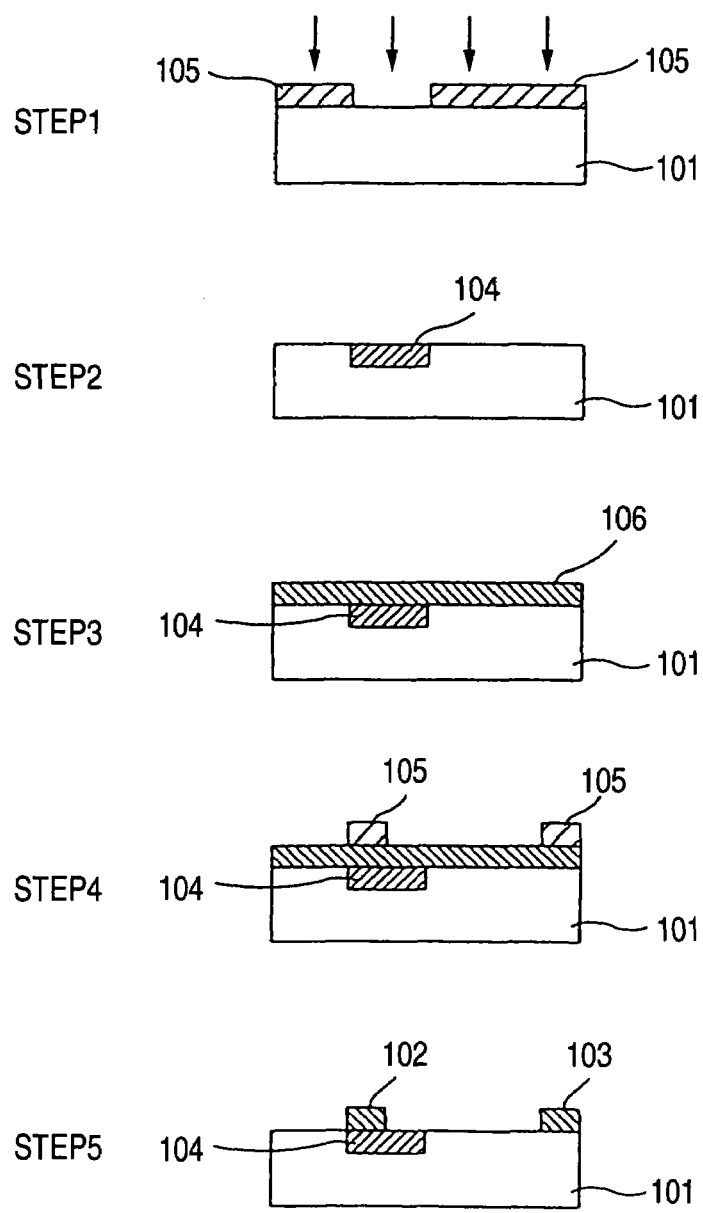
FIG. 2 is a view showing procedure for manufacturing the microphotodiode.

The microphotodiode 100 can be obtained by the following procedure. FIG. 2 shows procedure for manufacturing the microphotodiode 100.

A resist 105 is mounted on the p-type substrate 101 and an n-type impurity is implanted/diffused so that the n-type diffusion layer 104 is formed on the p-type substrate 101 (STEP 1 and STEP 2). Next, Al deposition for depositing a film 106 formed of aluminum is carried out over the p-type substrate 101 provided with the n-type diffusion layer 104 (STEP 3). Then, a resist 105 is provided on the film 106 in order to form an electrode pattern and etching is carried out to finish the microphotodiode 100 having the n-type electrode 102 and the p-type electrode 103 (STEP 4 and STEP 5).

Since the microphotodiode 100 is used while being embedded under a retina, it is preferable that one side should be approximately 1 μm to 100 μm. Although the microphotodiode 100 to be utilized in the embodiment uses the p-type substrate 101, it is not restricted. For example, an n-type substrate may be used to form an n-type electrode and a p-type electrode. While the aluminum is used as a conductive material in the embodiment, moreover, it is not restricted but a material having an excellent biocompatibility may be used. For example, platinum, gold, tungsten and titanium may be used.

Next, the structure of the irradiating device of the vision regeneration assisting apparatus will be described.

Figure 3:
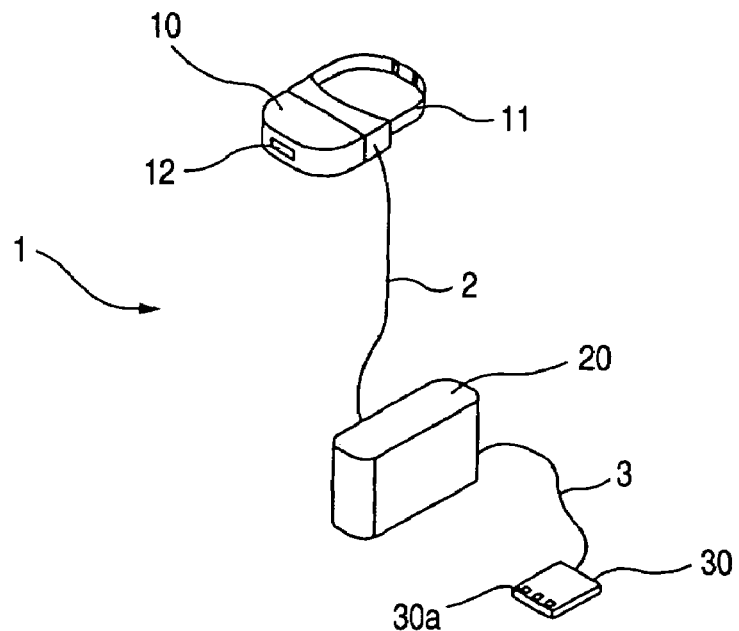
FIG. 3 is a view showing the schematic structure of the appearance of an irradiating device.

FIG. 3 is a view showing the schematic structure of the appearance of the irradiating device for applying a predetermined luminous flux on the microphotodiode 100 embedded under the retina of an eye E of a patient.

1 denotes an irradiating device body. The body 1 comprises a photographing unit 10, an image processing unit 20 and a response unit 30. The photographing unit 10 and the response unit 30 are connected to the image processing unit 20 through cables 2 and 3, respectively.

The photographing unit 10 takes the shape of goggles to be attached on the front of the eyes of the patient and can be fixed and held at the front of the eyes of the patient by using a belt 11. 12 denotes a photographing window for photographing an external world seen from the front of the eyes of the patient by using a CCD camera 13 provided in an inner part (which will be described below). The camera 13 is attached inside the photographing unit 10 in such a manner that a photographing axis of the camera 13 is coaxial with a visual axis set when the patient sees a thing in a horizontal direction.

While the attachment position of the camera 13 is placed in such a manner that the photographing axis of the camera 13 is coaxial with the visual axis set when the patient sees the thing in the horizontal direction as described above in the embodiment, it is not restricted but the photographing axis of the camera 13 is preferably adapted corresponding to a direction in which the patient can see the thing most easily.

Moreover, the photographing unit 10 also comprises an irradiating optical system for applying a predetermined luminous flux to the retina of the eye E based on the image (video) of the photographed external world in addition to the camera 13 (which will be described below).

The image processing unit 20 carries out a predetermined image processing over image information (video information) obtained by the photographing unit 10.

The response unit 30 is used for correcting the vision regeneration state of the patient attaching the photographing unit 10. 30a denotes a switch group for changing the characteristic and irradiation state of a luminous flux which is applied from the photographing unit 10. By using the switch group 30a, the vision regeneration state of the patient can be reflected on image processing to be carried out by the image processing unit 20 or the irradiating conditions of a luminous flux in the photographing unit 10.

Figure 4:
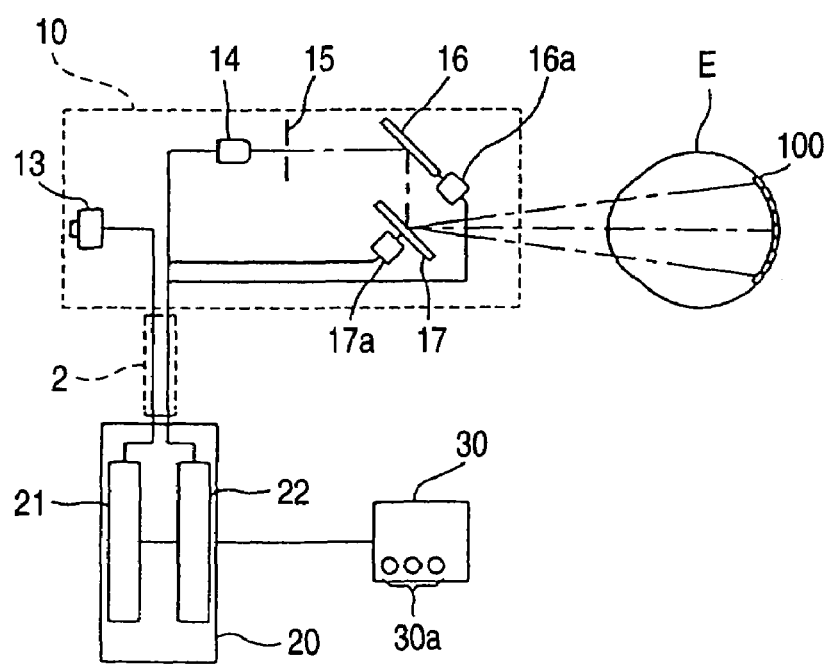
FIG. 4 is a view showing the schematic structure of an optical system and a control system in the irradiating device.

FIG. 4 is a view showing the schematic structure of an optical system and a control system in the body 1.

14 denotes an LED which serves to apply a white luminous flux having a great directivity based on a signal sent from the image processing unit 20. While the LED is used as a light source for irradiation on the microphotodiode in the embodiment, it is not restricted but can preferably apply a luminous flux having a large light quantity and directivity. For example, a semiconductor laser can also be used for the light source. Moreover, the wavelength of light to be applied is not restricted to a visible range but may be present in an infrared range.

15 denotes an aperture diaphragm by which a spot diameter of a luminous flux to be applied to a retina is reduced to be sufficiently small and a spot diameter of approximately several μm to several hundreds μm can be obtained over the retina. While the spot diameter of the luminous flux to be applied to the retina is determined by the aperture diaphragm 15 in the embodiment, it is not restricted but can also be determined by using an optical member such as a lens.

16 and 17 denote a mirror for guiding a luminous flux applied from the LED 14 onto the retina. Motors 16a and 17a are attached to the mirrors 16 and 17 respectively and the mirrors 16 and 17 are turned (swung) in a predetermined direction by the driving operations of the motors 16a and 17a. The luminous flux applied from the LED 14 is reflected by the mirrors 16 and 17 turned by means of the motors 16a and 17a and is scanned two-dimensionally over the retina in vertical and transverse directions.

21 denotes an image processing section for carrying out predetermined image processing over image information obtained from the camera 13. 22 denotes a control section for controlling the ON operation of the LED 14 and the driving operations of the motors 16a and 17a based on the image information converted in the image processing section 21.

Description will be given to the operation of the vision regeneration assisting apparatus having the structure described above.

First of all, an operator embeds a large number of microphotodiodes 100 in the retina of the eye E (a microphotodiode group including a large number of microphotodiodes is formed on a fundus). In the embodiment, the luminous flux applied from the LED 14 is scanned two-dimensionally for a large number of microphotodiodes 100. Consequently, the image information obtained by the camera 13 is reproduced so that vision is obtained.

Accordingly, a region on the retina in which the microphotodiodes 100 are embedded is to have such a sufficient size as to reproduce the whole photographing region of the camera 13, and furthermore, the embedding is preferably carried out throughout the whole region. The number of the microphotodiodes may be approximately 3×3 (9) or 5×5 (25) in respect of simple graphic recognition.

If an embedding interval between the microphotodiodes 100 is great, moreover, a portion in which light is not received by the microphotodiode 100 is formed in the scan of the luminous flux so that precise reproduction is hard to perform. Accordingly, it is preferable that the embedding interval between the microphotodiodes 100 should be smaller than the diameter of the luminous flux.

Next, the photographing unit 10 is attached at the front of the eyes of the patient to regenerate vision. In the embodiment, the photographing axis of the camera 13 is set to be coaxial with the visual axis obtained when the patient watches in a horizontal direction. For this reason, to change the vision, a watching direction is varied by a whole face without moving eyes. Consequently, the direction of the line of vision is almost coincident with the image of the external world photographed by the camera 13.

The image of the external world photographed by the camera 13 is transmitted to the image processing section 21 through the cable 2. The image processing section 21 carries out processing such as noise removal and smoothing over the image information thus transmitted (the quantity of light, the shades of colors and a hue). Moreover, the edge of the image is detected and the image of the photographed external world is converted into image representing only a contour.

Figure 5A:
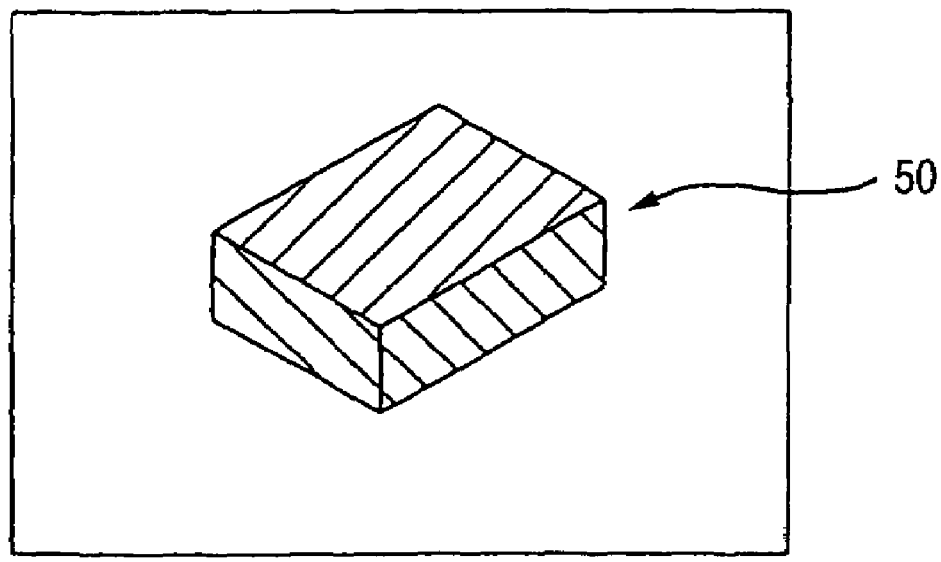
FIG. 5 is a view showing an example of image processing.
Figure 5B:
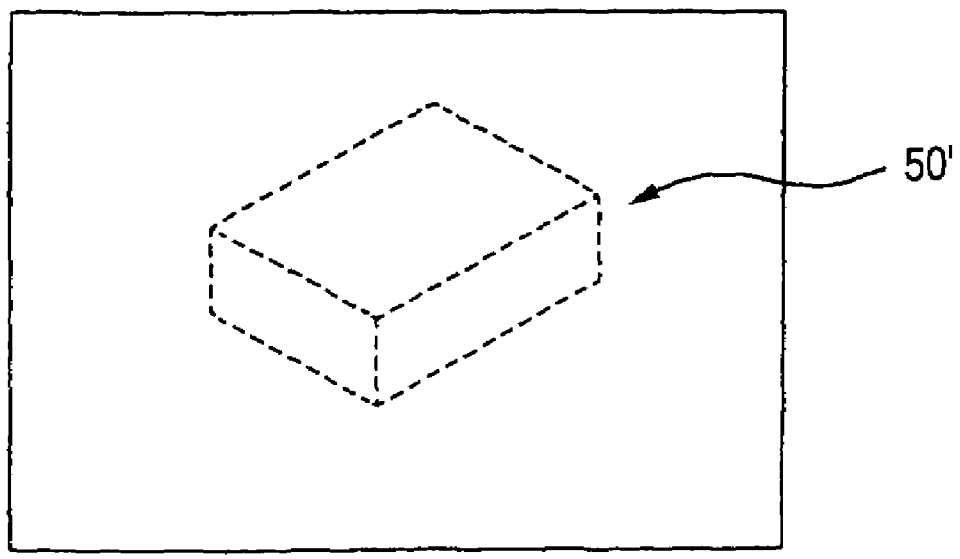

For example, in the case in which a box 50 taking the shape of a rectangular parallelepiped shown in FIG. 5(a) is photographed by the camera 13 of the photographing unit 10, a color and a pattern are removed from the image information of the box 50 by the image processing of the image processing section 21 and the same image information is converted into image information (a box 50') representing only the contour of the box 50 (a dotted-line portion).

The image processing is carried out by the image processing section 21 and the image information thus processed (the image representing only the contour) is transmitted to the control section 22. The control section 22 converts the processed image information into an electric pulse signal to control the ON operation of the LED 14. At the same time, the control section 22 controls the driving operations of the motors 16a and 17a to scan an applied luminous flux in such a manner that the image representing only the contour can be reproduced by the luminous flux within the range of the microphotodiode 100 embedded on the retina.

At this time, the control section 22 applies a luminous flux emitted from the LED 14 as pulse light to the microphotodiode 100. The pulse waveform of the luminous flux serves to induce the excitation of the nerve cell of the retina which is necessary for the perception of vision.

The microphotodiode 100 receives the pulse light from the LED 14 and converts the pulse waveform into an electric signal. The electric signal is transmitted to a brain through an optic nerve so that the vision can be obtained.

The lighting conditions (irradiating conditions) of the optical pulse emitted from the LED 14, for example, a frequency and an amplitude (a light quantity) of the optical pulse and a time interval for the lighting can be changed corresponding to each pixel unit by the switch group 30a of the response unit 30.

The amplitude is preferably set in such a manner that the current value of the electric signal generated from the microphotodiode 100 on the receiving side ranges from 10 μA to 6 mA. When the current value of the electric signal generated from the microphotodiode 100 is less than 10 μA, electric stimulation is reduced. When the current value is more than 6 mA, moreover, the electric stimulation is excessively increased so that the muscular twitch of the eye might be caused.

Furthermore, the repetitive frequency of the scan can also be changed by the switch group 30a. By varying the repetitive frequency, it is possible to change the condition of a flicker of the reproduced image. It is preferable that the repetitive frequency should range from 25 Hz to 100 Hz. When the repetitive frequency is less than 25 Hz, the flicker of an image is increased so that a feeling of physical disorder is generated. When the repetitive frequency is more than 100 Hz, moreover, it is faster than the speed of the excitation response of a cell so that reaction cannot be accepted.

A patient can use the switch group 30a of the response unit 30 to change the irradiating conditions of the pulse light and the repetitive frequency of the scan, thereby setting the condition on which vision can be obtained most easily for himself (herself).

The contents thus set are transmitted to the control section 22 through the cable 3. The control section 22 controls the ON operation of the LED 14 and the driving operations of the motors 16a and 17a in accordance with the set conditions.

In the embodiment, thus, photoelectric conversion to be conventionally carried out in a photoreceptor cell is performed by the photodiode and the formation of a pulse to excite a ganglion cell is carried out by an external device. Even if the photoreceptor cell is decreased so that vision is lost, therefore, it is not necessary to use a photosensor having a complicated mechanism for compensating for the vision. It is sufficient that the microphotodiode 100 has the function of simply converting an optical signal into an electric signal.

While the luminous flux applied from the LED 14 is changed into a pulse waveform and is scanned for the microphotodiode 100 in the embodiment, it is also possible to obtain the same advantages by properly changing the repetitive frequency of the scan using continuous light, thereby varying a time taken for applying the luminous flux per unit area.

In the embodiment, moreover, the image of an object which is photographed is not seen through a monitor such as a CRT or an LCD but the object is reproduced on the retina by the scan of the luminous flux. By detecting the distance of the object to be photographed by an image processing and variously changing the lighting conditions of pulse light to be applied for the distance of each object to be photographed, therefore, it is possible to emphasize the distance of the object.

Figure 6:
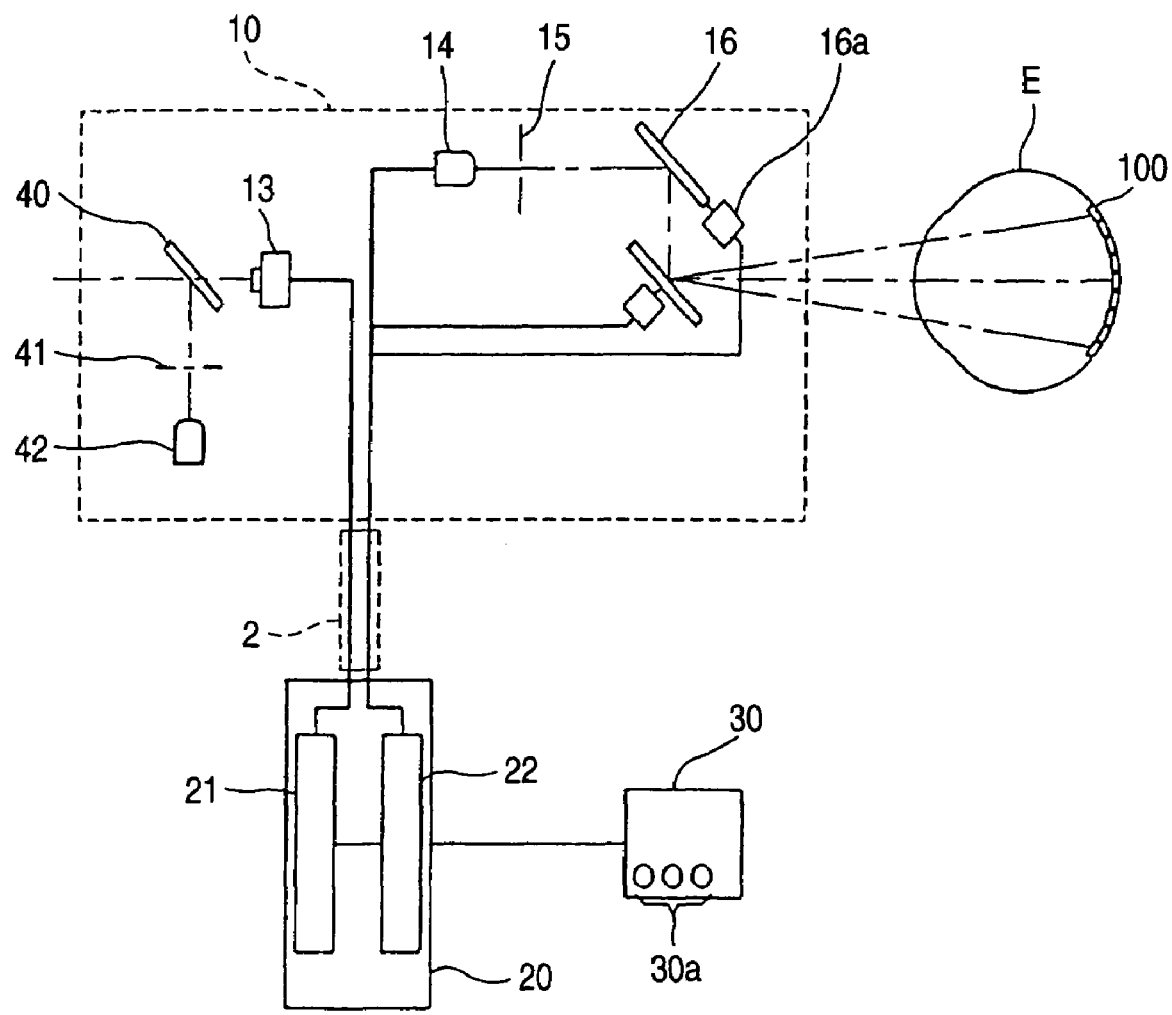
FIG. 6 is a view showing the schematic structure of the optical system and the control system in the irradiating device for detecting the distance of an object.

FIG. 6 shows a vision regeneration assisting apparatus having a structure for detecting the distance of an object. The portions having the same reference numerals as those in FIG. 4 have the same functions.

40 denotes a half mirror to be put on the photographing axis of the camera 13. 41 denotes an aperture provided with an opening portion having a regular pattern (a grid pattern). 42 denotes a light source. An illuminating luminous flux emitted from the light source 42 projects a luminous flux having the grid pattern onto an object before the eyes through the half mirror 40 and forms the grid pattern on the surface of the object.

The image processing section 21 prestores the size of a grid pattern to be formed at a predetermined distance (for example, 1 m) and stereo information and distance information can be obtained from the shape (size, strain) of the grid pattern projected onto the object to be photographed by the camera 13.

The image processing section 21 obtains the stereo information and the distance information depending on the state of the grid pattern formed on the surface of the object and transmits them to the control section 22 together with the image information obtained by the image processing (contour extraction). The control section 22 detects the distance of the object based on the obtained image information and changes the lighting conditions of pulse light emitted from the LED 14 depending on the distance of each object, thereby reproducing the contour of the object on the microphotodiode 100.

For example, the lighting interval of the LED 14 is reduced (a cycle is shortened) to reproduce the contour of a close object portion, thereby giving more simulation, and the lighting interval of the LED 14 is increased (the cycle is prolonged) to reproduce the contour of a distant object portion, thereby reducing the stimulation. Thus, information about a distance can be given for each object by a texture (pattern) projecting method.

While the lighting conditions of the pulse light emitted from the LED 14 are thus changed based on the distance of the object to be photographed, various information about the color and material of the object can also be used as means for giving recognition to a patient depending on a change in the lighting condition, for example.

While the luminous flux is scanned by using the driving mirror in the embodiment, it is sufficient that the luminous flux for forming an image processed by the image processing means is applied toward the microphotosensor.

FIG. 7 is a view showing an embodiment in which the invention is applied by using a digital micromirror device (DMDTM manufactured by Texas Instruments Co., Ltd.). The portions having the same reference numerals as those shown in FIG. 4 have the same functions and description will be omitted.

Figure 7A:
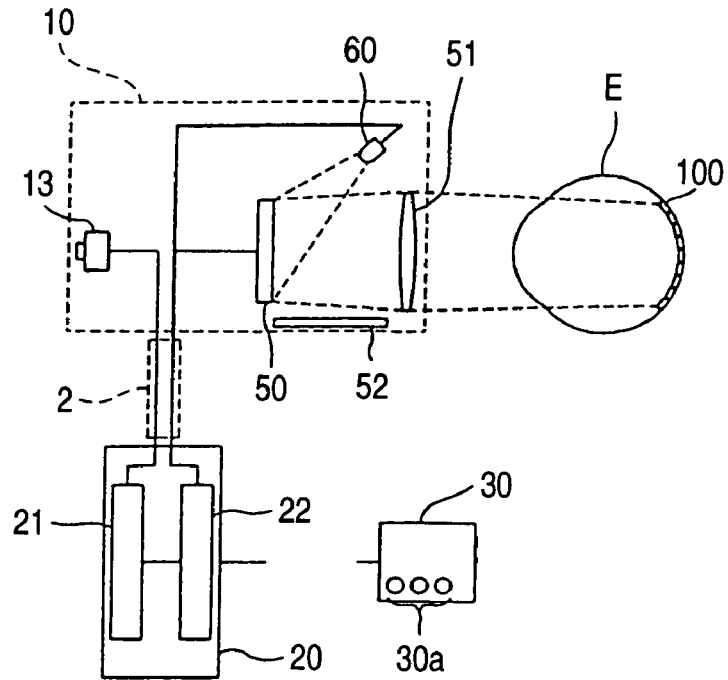
FIG. 7 is a view showing another embodiment of the irradiating device.

In FIG. 7(a), 50 denotes a digital micromirror device, 51 denotes a lens, 52 denotes a light absorbing plate, and 60 denotes a light source for applying illuminating light onto the whole digital micromirror device. The digital micromirror device 50 is provided in such a position as to be conjugated with the light receiving surface of the microphotodiode 100 through the lens 51 in the photographing unit 10.

Figure 7B:
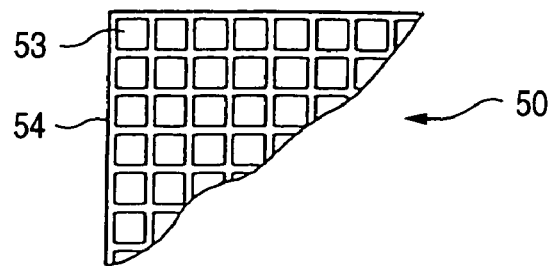

FIG. 7(b) is an enlarged view showing a part of the digital micromirror device 50. 53 denotes a micromirror having a size of approximately 16 μm square. 54 denotes a base fixing and holding the micromirror 53 inclinably at a predetermined angle. 500,000 micromirrors 53 or more are fixed and held on the base 54 and an interval between the micromirrors 53 is less than 1 μm. Moreover, the micromirror 53 is inclined at +10 degrees by adding an electrostatic charge (turning ON) and is inclined at −10 degrees by removing the charge (turning OFF). The ON/OFF of the charge can be carried out 5000 times per second. Consequently, the micromirror 53 can be switched quickly at a predetermined angle.

Figure 7C:
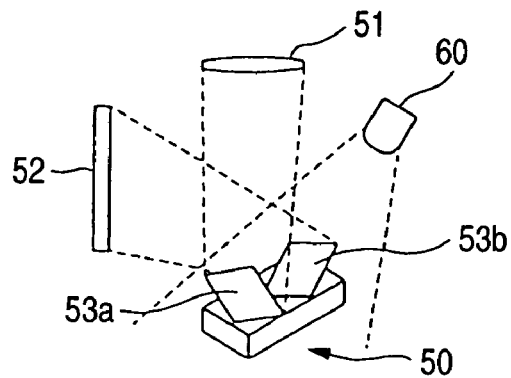

A method of forming an image by using the digital micromirror device 50 will be described with reference to FIG. 7(c). In FIG. 7(c), the digital micromirror device 50 using two micromirrors 53a and 53b is utilized.

An illuminating luminous flux emitted from the light source 60 illuminates the whole digital micromirror device 50. The micromirror 53a to which the electrostatic charge is given is inclined at +10 degrees and a luminous flux reflected by a reflecting surface passes through the lens 51. On the other hand, the micromirror 53b to which the charge is not given is inclined at −10 degrees and a luminous flux reflected by a reflecting surface does not pass through the lens 51 but is transmitted toward the light absorbing plate 52. Thus, it is possible to transmit the image information to the eyes of the patient through the lens 51 by giving the charge to only the micromirror 53 required for (corresponding to) the formation of an image.

In the structure using the digital micromirror device 50 described above, an operation thereof will be described with reference to FIG. 7(a).

The image of the external world photographed by the camera 13 is transmitted to the image processing section 21 through the cable 2. The image processing section 21 carries out processing such as noise removal and smoothing over the image information thus transmitted (the quantity of a light, the shades of colors and a hue). Moreover, the edge of the image is detected and the image of the photographed external world is converted into an image representing only a contour, and the same image is transmitted to the control section 22. The control section 22 gives a charge to the micromirror 53 of the digital micromirror device 50 to be driven in such a manner that the processed image information is received by the microphotodiode 100 based on the same image information.

The light source 60 illuminates the whole digital micromirror device 50 and an image is formed depending on only a difference in the inclination angle of the micromirror 53. Moreover, the control section 22 further turns ON/OFF the charge with respect to the micromirror 53 giving the charge and converts the image information into a pulse signal. By such a method, it is possible to control a frequency to be a pulse signal having a preferable waveform for stimulating a ganglion cell or a lighting time interval. Moreover, the amplitude (the light quantity) can be changed by the light source 60.

As means for applying the image information on the eyes of the patient, moreover, it is also possible to use a structure in which a large number of LEDs are arranged in place of the digital micromirror device.

Figure 8:
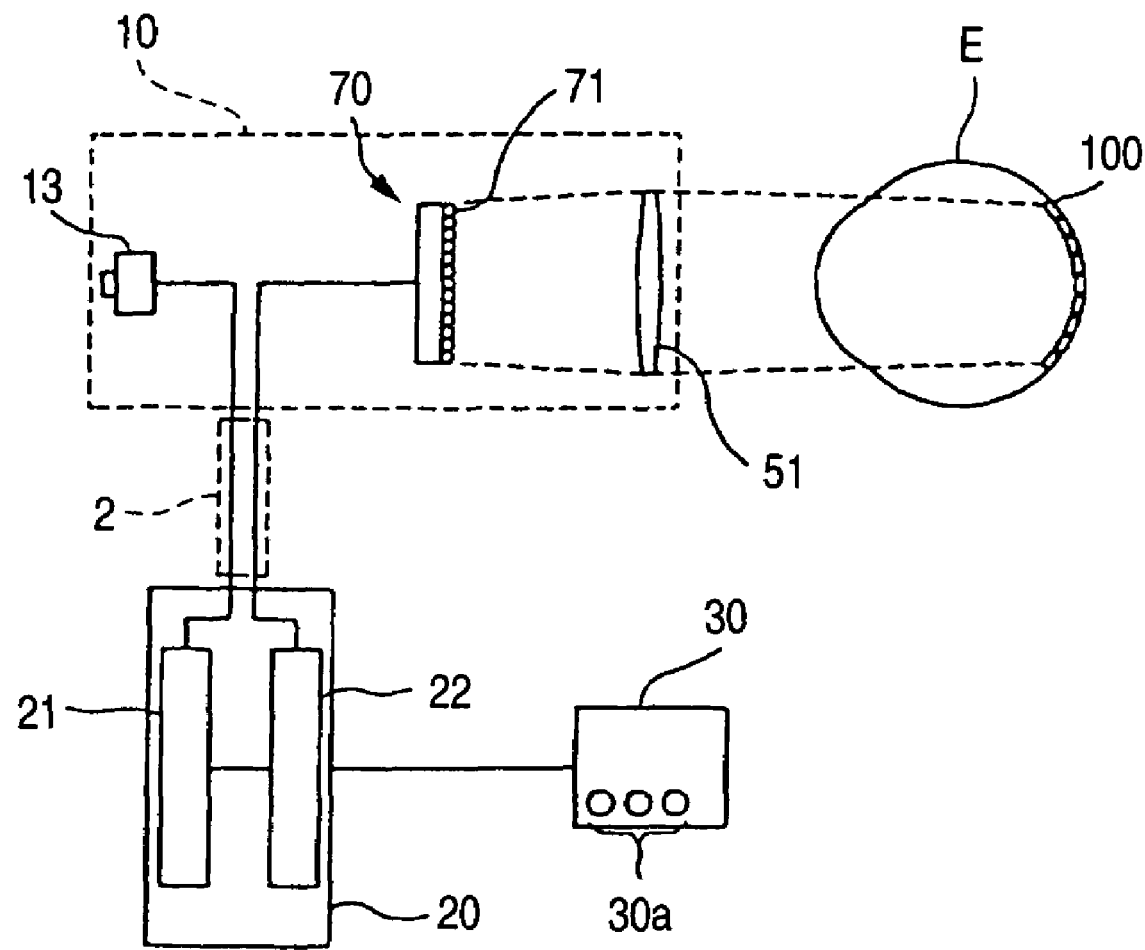
FIG. 8 is a view showing a further embodiment of the irradiating device.

FIG. 8 is a view showing a structure using a large number of LEDs as irradiating means.

70 denotes display means in which a large number of LEDs 71 are arranged two-dimensionally. Image information photographed by the camera 13 is subjected to predetermined processing by the image processing section 21 and is then transmitted to the control section 22. The control section 22 controls to turn ON each of the LEDs 71 and displays an image on the display means 70 based on the processed image information. By flashing the LED 71 or regulating the quantity of light through the control section 22, moreover, it is possible to generate a pulse signal having a preferable waveform for stimulating the ganglion cell.

While the invention has been described in detail with reference to the specific embodiment, it is apparent to the skilled in the art that various changes and modifications can be made without departing from the spirit and scope of the invention.

The application is based on Japanese Patent Application (No. 2001-039031) filed on Feb. 15, 2001 and Japanese Patent Application (No. 2001-267743) filed on Sep. 4, 2001 and the contents are incorporated herein by reference.

INDUSTRIAL APPLICABILITY

As described above, in the invention, a work which has conventionally been carried out in eyes can be performed on the outside and a photosensor to be embedded in a retina which has only the function of simply converting an optical signal into an electric signal can be used. Consequently, it is possible to assist in the regeneration of a vision without using a complicated system.

The invention claimed is:

1. A vision regeneration assisting apparatus for regenerating vision of a patient going blind by a disease of a retina, comprising:
    a photosensor to be embedded in the retina of an eye of the patient and for converting an optical signal into an electric signal;
    photographing means for photographing an object to be recognized by the patient;
    image processing means for carrying out image processing on an image of the photographed object to detect an edge of the image and obtaining an image representing only a contour of the object;
    irradiating means for irradiating pulse light having a pulse waveform serving to induce excitation of a nerve cell of the retina which is necessary for perception of vision
    scanning means provided at the front of the eye of the patient for two-dimensionally scanning the irradiated light over the photosensor; and
    control means for controlling the irradiating means and the scanning means based on image information obtained by the image processing means; and
    wherein the scanning means includes a pair of mirrors and a pair of motors for driving the pair of mirrors; and
    wherein the control means controls driving operation of the pair of motors based on the image information.

2. The vision regeneration assisting apparatus according to claim 1, wherein the control means controls a repetitive frequency of the scan.

3. The vision regeneration assisting apparatus according to claim 1, wherein a plurality of photosensors are to be embedded in the retina of the eye of the patient and an embedding interval between the photosensors is smaller than a spot diameter of the light on the photosensor.

4. The vision regeneration assisting apparatus according to claim 1, further comprising changing means for changing an irradiating condition of the light by the irradiating means,
    wherein the control means controls the irradiating means based on the changed irradiating condition.

5. The vision regeneration assisting apparatus according to claim 1, further comprising projecting means for projecting a predetermined pattern onto the object.

6. The vision regeneration assisting apparatus according to claim 1, wherein
    the irradiating means irradiates the pulse light, and
    the control means controls at least one of a frequency and an amplitude of the pulse light based on the image information.

7. A vision regeneration assisting apparatus for regenerating vision of a patient going blind by a disease of a retina, comprising:
    a photosensor to be embedded in the retina of an eye of the patient and for converting an optical signal into an electric signal;
    a camera that photographs an object to be recognized by the patient;
    a processor that processes on an image of the photographed object to detect an edge of the image and obtain an image representing only a contour of the object;
    a light source that irradiates pulse light having a pulse waveform that induces excitation of a nerve cell of the retina for perception of vision;
    a scanner at the front of the eye of the patient that two-dimensionally scans the irradiated light over the photosensor; and
    a controller that controls the light source and the scanner based on image information obtained by the processor; and
    wherein the scanner includes a pair of mirrors and a pair of motors for driving the pair of mirrors; and
    wherein the controller controls driving operation of the pair of motors based on the image information.

* * * * *